United States Patent [19]

Bradford

[11] Patent Number: Plant 6,982

[45] **Date of Patent: * Aug. 15, 1989**

[54] DWARF NECTARINE TREE (RED SUNSET)

[76] Inventor: Norman G. Bradford, 11875 Savana Rd., Le Grand, Calif. 95333

[ * ] Notice: The portion of the term of this patent subsequent to Nov. 15, 2003 has been disclaimed.

[21] Appl. No.: 702,917

[22] Filed: Feb. 19, 1985

[51] Int. Cl.[4] ..... A01H 5/00
[52] U.S. Cl. ..... Plt./41
[58] Field of Search ..... Plt./41

*Primary Examiner*—Robert E. Bagwill
*Attorney, Agent, or Firm*—Worrel & Worrel

[57] ABSTRACT

A new and distinct variety of Nectarine Tree which is somewhat similar to the May Grand Nectarine Tree, U.S. Plant Pat. No. 2,794, with which it is most closely related, but which is distinguished therefrom and characterized as to novelty by producing fruit which is ripe for commercial harvesting eight days later than the May Grand Nectarine Tree and is a genetic dwarf tree.

1 Drawing Sheet

BACKGROUND OF THE NEW VARIETY

The present invention relates to a new and distinct variety of nectarine tree to be known as Red Sunset and more particularly to a new and distinct genetic dwarf variety broadly characterized by a vigorous, spreading tree which reaches six feet in height and bears freestone fruit possessing many of the characteristics of color, size, firmness and flavor generally found in nectarine fruit produced by full size trees. The fruit ripens the middle of June under the ecological conditions described, in the San Joaquin Valley of California and is of medium size when compared to fruit of other genetic dwarf nectarine trees.

The fruit of the instant variety of genetic dwarf nectarine tree most nearly resembles the genetically tall May Grand variety (U.S. Plant Pat. No. 2,794), but ripens about nine days later.

This variety was propagated by me at Bradford Farms in Merced County, Calif., as the second generation from a cross of an unnamed genetic dwarf seedling as a seed parent by May Grand (U.S. Plant Pat. No. 2,794), a tall nectarine variety, as a pollen parent. I asexually reproduced the resulting plant by budding and grafting, and such reproduction of plant and fruit characteristics were true to the original plant in all respects.

BRIEF DESCRIPTION OF THE DRAWING

The accompanying photographic includes different views of whole fruits, showing the characteristics of skin color and form, and a characteristic fruit divided on its suture plane showing the flesh color and the stone cavity thereof, and two stones all of the subject variety.

DETAILED DESCRIPTION

Referring now more specifically to the pomological characteristics of this new and distinct variety of genetic dwarf nectarine tree, the following has been observed by me under the ecological conditions prevailing near LeGrand, Merced County (San Joaquin Valley), Calif. All color plate identifications are by reference to the Inter-Society Color Council, National Bureau of Standards. Common color names are also used occasionally.

TREE

General: Hardy, vigorous, productive and regular bearing.

*Form.*—Dense, spreading, round topped depending upon pruning practices.

*Size.*—Six feet tall at maturity, an average size for a genetic dwarf.

Trunk:

*Size.*—Medium.

*Texture.*—Shaggy.

*Lenticels.*—Numbers — few, approximately 3/16 inch, [4.762 mm] in diameter; Color — Brown, [46. gy r Br.].

*Branches.*—Medium in size with shaggy brown bark on 2nd year and older wood and green bark on first year wood. A few small lenticles may be present. — Color — first year wood — yellow-green, [116. brill. Y G]; Color — second year wood-brown, [56. deep Br].

Leaves:

*Size.*—Length — approximately 5½ inches, [1.39.7 mm]; Width — approximately 1⅛ inches, [28.75 mm].

*Form.*—Elliptical.

*Base.*—Acute.

*Apex.*—Acuminate.

*Margin.*—Crenate to finely serrate.

*Venation.*—Pinnately net veined.

*Petiole.*—Long, average length approximately ¾ inch. [19.050 mm].

*Glands.*—Reniform.

*Stipules.*—Numbers — numerous; Length — long, approximately ¼ inch, [6.35 mm]; Numbers — generally — two per leaf.

*Color.*—Dorsal surface — green, [126. d. Ol G], occasionally some leaves may be found having a light purple color. Ventral surface — light green [120. m YG].

*Leaf buds.*—Pointed.

Flowers:

*Buds.*—Hardy, medium in size, medium in length, obtuse, plump, free, pubescent.

*Flowers.*—Blooming date — average as compared with other varieties. Size: Generally — large. Color: Generally — pink, the color of the flower is not particularly distinctive of the subject variety.

FRUIT

Maturity when described: Ripe for commercial harvesting approximately, June 27, 1984.

Size:

*Generally.*—Medium.

*Uniformity.*—Uniform.

*Axial diameter.*—Approximately 2⅝ inches, [66.675 mm.].

*Diameter in suture plane.*—Approximately 2⅛ inches, [53.975 mm].

Form: Uniform, symmetrical.

*Form.*—Longitudinal section — slightly oblong; form — transverse through the diameter — slightly oval with suture area protruding.

Suture: An inconspicuous line that becomes distinct near the apex, which extends from the base to beyond apex with a slight depression before the pistil point.

Surface: Ventral surface rounded throughout on both sides, lips appear somewhat equal.

Cavity: Rounded, slightly elongated in the suture plane, the suture appears on both sides, stem attachment marks are evident.

*Depth.*—Approximately ⅜ inch [9.525 mm].

*Breadth.*—Approximately ⅜ inch [9.525 mm].

Base: Slightly oblique on most fruit due to the stem attachment.

Apex: Short, rounded.

Pistil Point: Variable, both apical and oblique.

*Size.*—Generally — medium; length — approximately 5/16 inch, [7.938 mm]; width — approximately 3/16 inch, [4.762 mm].

Skin: Thin, tender, tenacious to flesh — free. Strong tendancy to crack in wet season.

Flesh:

*Color.*—Yellow to pit [83. brill Y]. Surface of pit cavity pink [28.1. Y Pink] some yellow fibers are evident, [83. brill Y].

*Texture.*—Soft, melting.

*Fibers.*—Few, fine, tender.

*Ripens.*—Fairly evenly.

*Flavor.*—Subacid.

*Aroma.*—Very slight.

*Amygdalin.*—Scarce, abundant juice.

*Eating quality.*—Very good when tree ripened.

STONE

Type: Freestone.

Form: Oblong.

*Color.*—Brown, [58. m. Br].

Base: Straight.

Hilum: Narrow.

Apex: Very sharp, unequal sides, curved on right. Apex is very sharp.

*Length.*—Approximately ⅛ inch, [3.175 mm].

Surface: Irregularly furrowed toward apex.

Ridges: Jagged toward the apex.

Thickness of pit wall: Approximately 3/16 of an inch, [4.762 mm].

Tendency to split is slight.

Kernel: Oval in form, bitter taste, viable.

*Width.*—Approximately 7/16 of an inch [11.112 mm].

*Length.*—Approximately ⅝ of an inch, [15.875 mm].

Pellicle: Yellow.

Amygdalin: Abundant.

Although the new variety of nectarine tree possesses the described characteristics when grown under the ecological conditions prevailing in LeGrand, Calif., in the central part of the San Joaquin Valley, it is to be understood that variations of the usual magnitude and characteristics incident to changes in growing conditions, fertilization, pruning and pest control are to be expected.

Having thus described and illustrated my new variety of Nectarine Tree, what is new and desired to be secured by Letters Patent is:

1. A new and distinct variety of genetic dwarf freestone nectarine tree, substantially as illustrated and described, which most closely resembles the genetically tall May Grand Nectarine Tree variety (U.S. Plant Pat. No. 2,794), but is distinguishable therefrom in that it ripens eight days later, yields a good flavored freestone nectarine fruit and is a genetic dwarf tree.

* * * * *

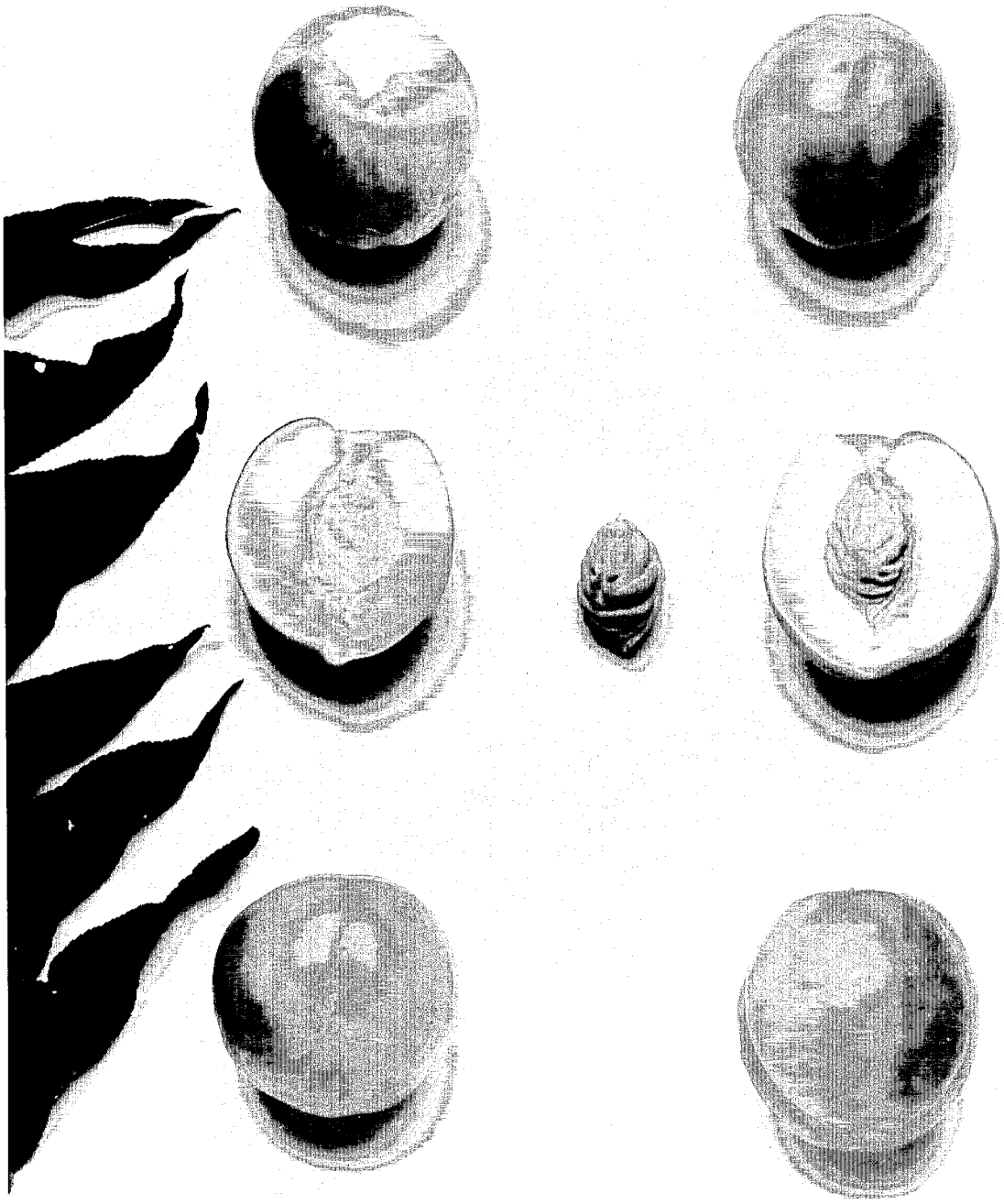

UNITED STATES PATENT AND TRADEMARK OFFICE

CERTIFICATE OF CORRECTION

PATENT NO. : PP 6,982

DATED : August 15, 1989

INVENTOR(S) : Norman G. Bradford

It is certified that error appears in the above-identified patent and that said Letters Patent is hereby corrected as shown below:

Change title from "DWARF NECTARINE TREE (RED SUNSET)

to ---DWARF NECTARINE TREE "RED SUNSET"

Column 3, Line 19

After "," insert ---and---

Column 4, Line 7

After "oblong" insert ---;---

Signed and Sealed this

Nineteenth Day of June, 1990

*Attest:*

*Attesting Officer*

HARRY F. MANBECK, JR.

*Commissioner of Patents and Trademarks*